United States Patent [19]

Halbich

[11] Patent Number: 5,522,503
[45] Date of Patent: Jun. 4, 1996

[54] SYRINGE CASE

[76] Inventor: Frank Halbich, W. 4595 Selway Ave., Post Falls, Id. 83854

[21] Appl. No.: 360,991

[22] Filed: Dec. 20, 1994

[51] Int. Cl.$^6$ ................................................. B65D 85/20
[52] U.S. Cl. ......................... 206/366; 206/815; 220/260; 220/339
[58] Field of Search ................................ 206/214, 365, 206/366, 370, 443, 815, 538, 539; 220/339, 524, 326, 260

[56] References Cited

U.S. PATENT DOCUMENTS

| | | | |
|---|---|---|---|
| 2,084,540 | 1/1937 | Smith | 206/43 |
| 2,110,123 | 3/1938 | Eisele | 206/43 |
| 2,604,987 | 7/1952 | Kolodny | 206/63.2 |
| 2,887,215 | 3/1959 | Hutchison | 206/17.5 |
| 2,955,705 | 10/1960 | Krueger | 206/43 |
| 3,146,935 | 9/1964 | Carkhuff et al. | 206/815 |
| 3,305,084 | 2/1967 | Higgins | 206/56 |
| 3,394,838 | 7/1968 | Larkin | 220/60 |
| 3,406,686 | 10/1968 | Keller | 128/218 |
| 3,489,268 | 1/1970 | Meierhoefer | 206/17.5 |
| 3,491,914 | 1/1970 | Elzey | 220/60 |
| 4,015,709 | 4/1977 | Millet | 206/366 |
| 4,223,787 | 9/1980 | Lowry | 206/387 |
| 4,314,637 | 2/1982 | Posso | 206/387 |
| 4,344,646 | 8/1982 | Michel | 292/87 |
| 4,366,915 | 1/1983 | Seidler | 220/339 |
| 4,383,615 | 3/1983 | Aquino | 211/60 |
| 4,469,225 | 9/1984 | Takahashi | 206/387 |
| 4,541,528 | 9/1985 | Holmes | 220/339 |
| 4,671,408 | 6/1987 | Raines | 206/365 |
| 4,753,345 | 6/1988 | Goodsir | 206/366 |
| 4,793,492 | 12/1988 | Halbich | 206/538 |
| 4,799,604 | 1/1989 | Okojima | 220/260 |
| 4,805,769 | 2/1989 | Soltis | 206/309 |
| 4,890,742 | 1/1990 | Allison | 206/540 |
| 5,074,848 | 12/1991 | Burt et al. | 604/263 |
| 5,311,990 | 5/1994 | Kalinski | 206/370 |

Primary Examiner—Jimmy G. Foster
Attorney, Agent, or Firm—Wells, St. John, Roberts, Gregory & Matkin

[57] ABSTRACT

A syringe case includes, a) a plurality of longitudinally elongated individual syringe retaining compartments having respective lengths which are greater than the length of a syringe for which the respective compartments are adapted; b) a separately openable and closable associated with the compartments, the lids include respective pairs of recesses provided in their opposing longitudinal edges, one longitudinal edge recess of one of the lids being longitudinally positioned to align with one longitudinal recess of the other lid to provide a finger space between the two juxtaposed lids, the finger space having a size sufficiently great to receive a human finger therewithin; c) at least one longitudinal hinge associated with the respective lids and compartments to support the respective lids for longitudinal swinging movement between open and closed positions relative to their respective compartments, the lid when closed defines a compartment volume which is sufficiently great to receive a syringe for which the compartment is adapted for sliding longitudinal movement within prescribed limits within the compartment, the prescribed limits are defined by a pair of opposing lid and floor projections; and d) a lid closure latch associated with the respective lids. Single syringe retaining cases are also disclosed.

29 Claims, 9 Drawing Sheets

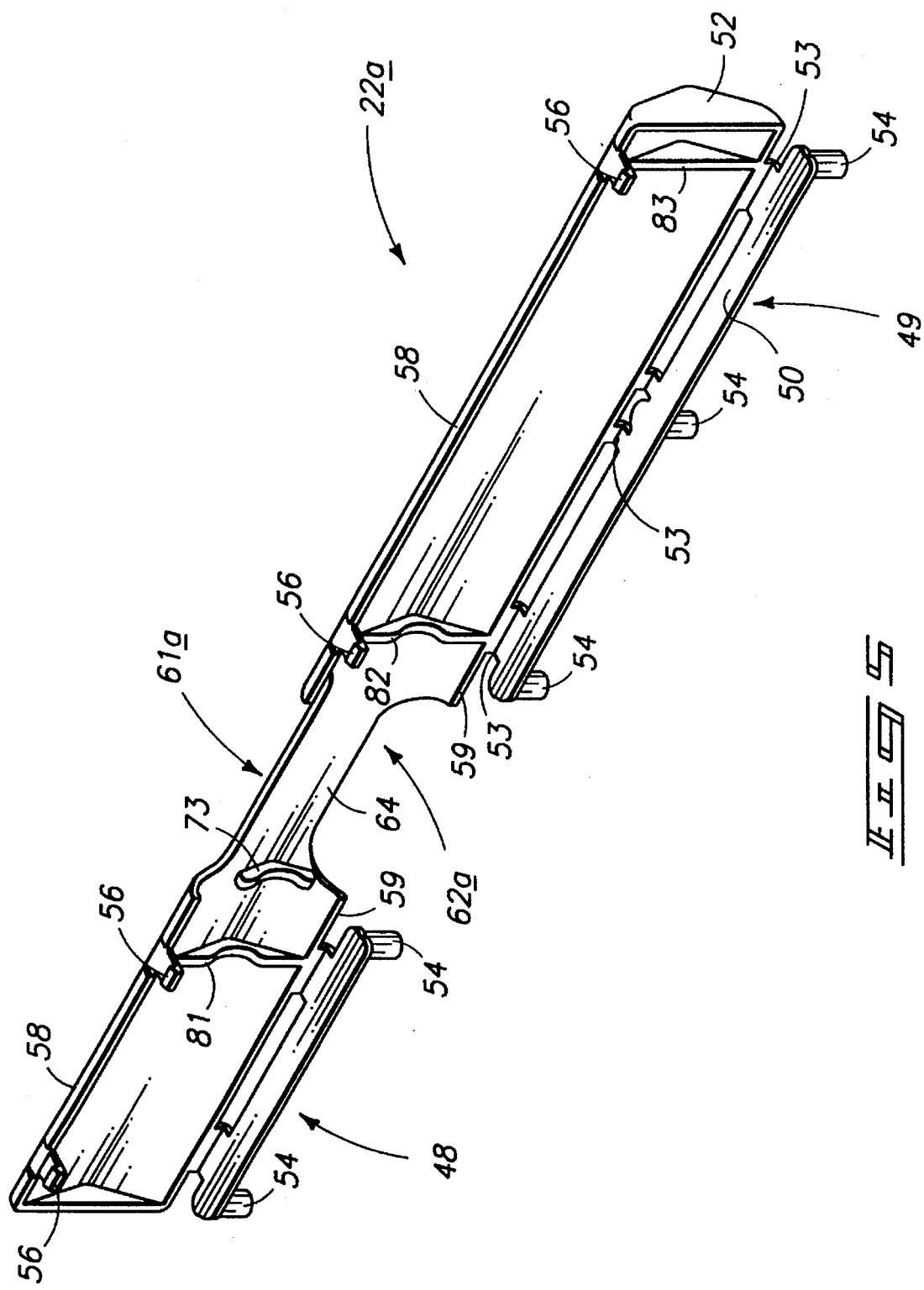

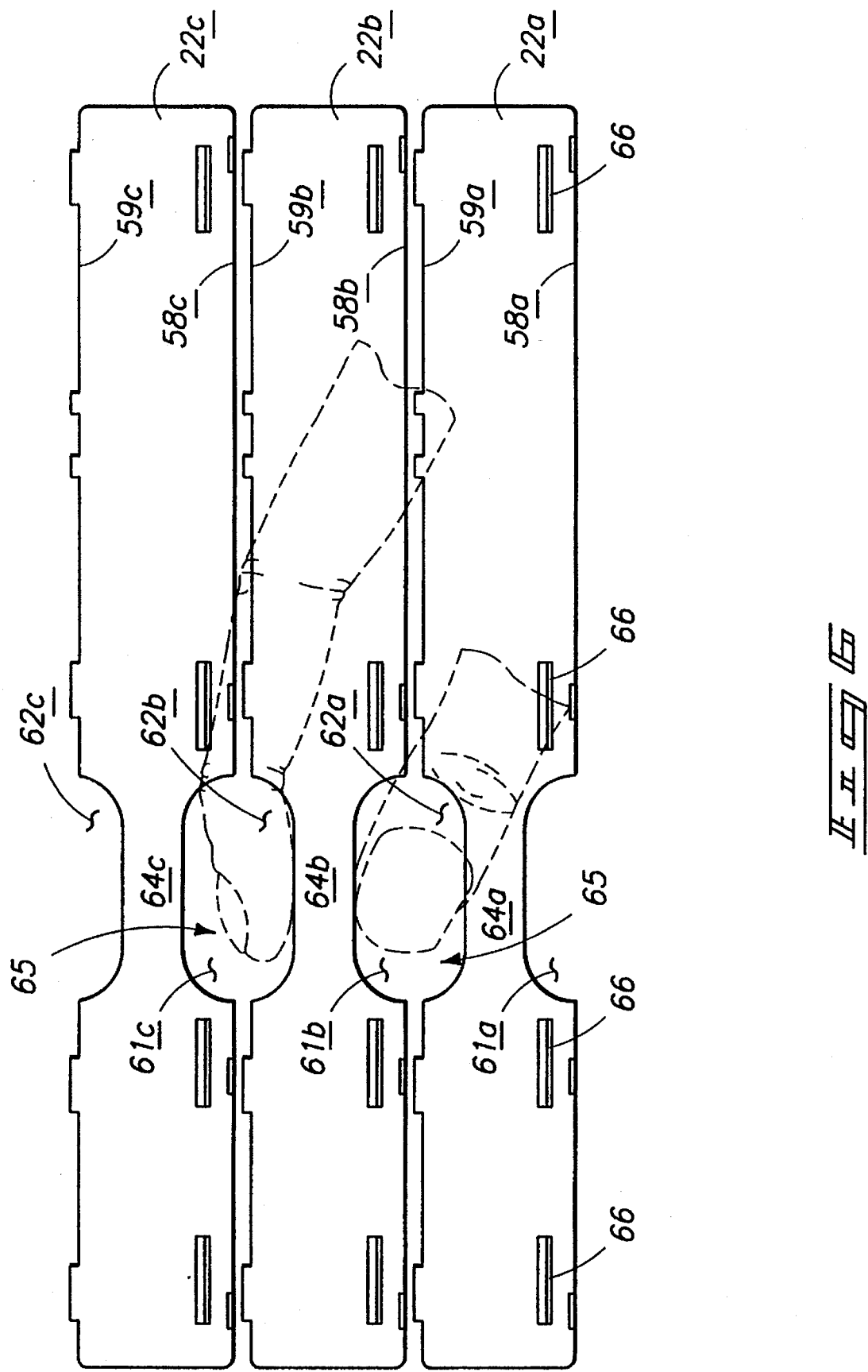

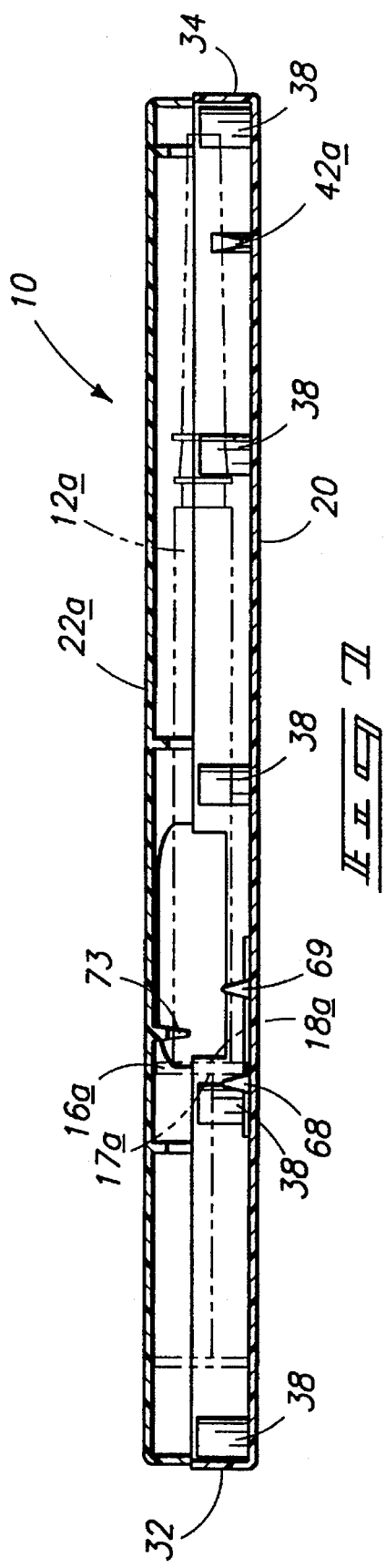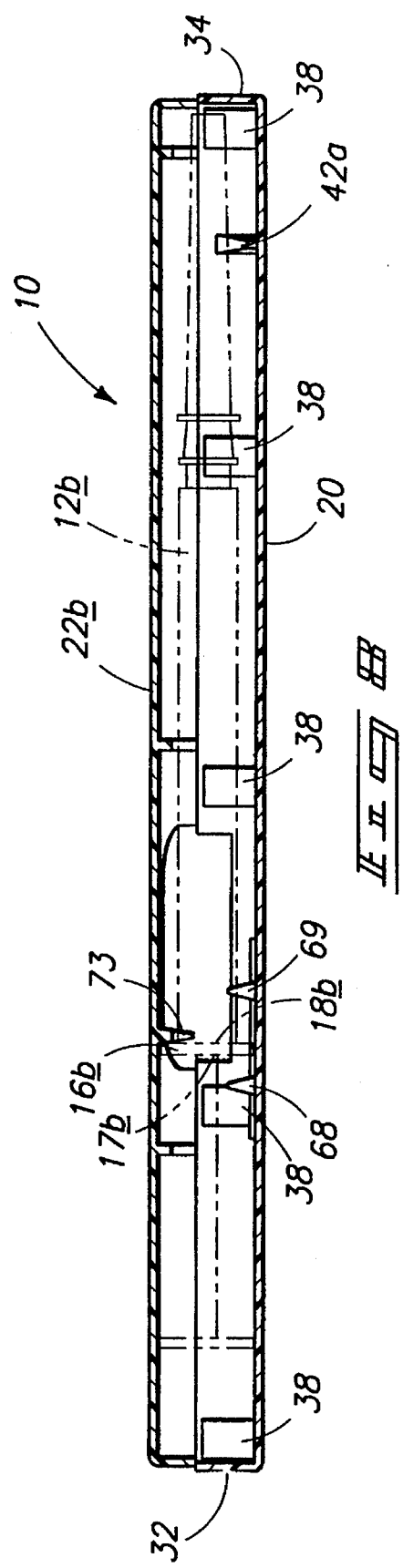

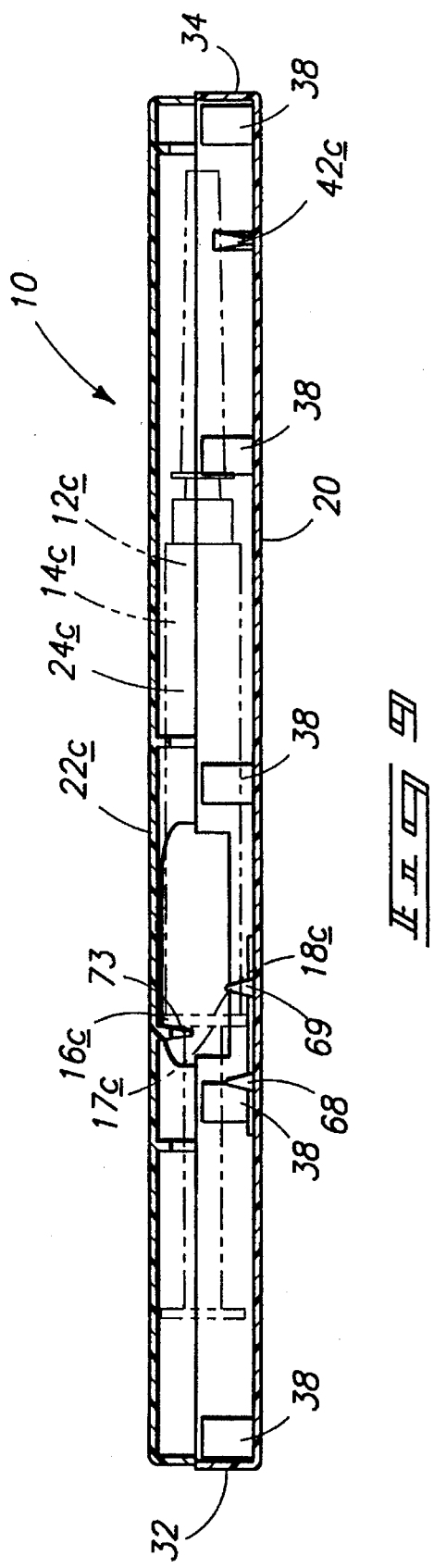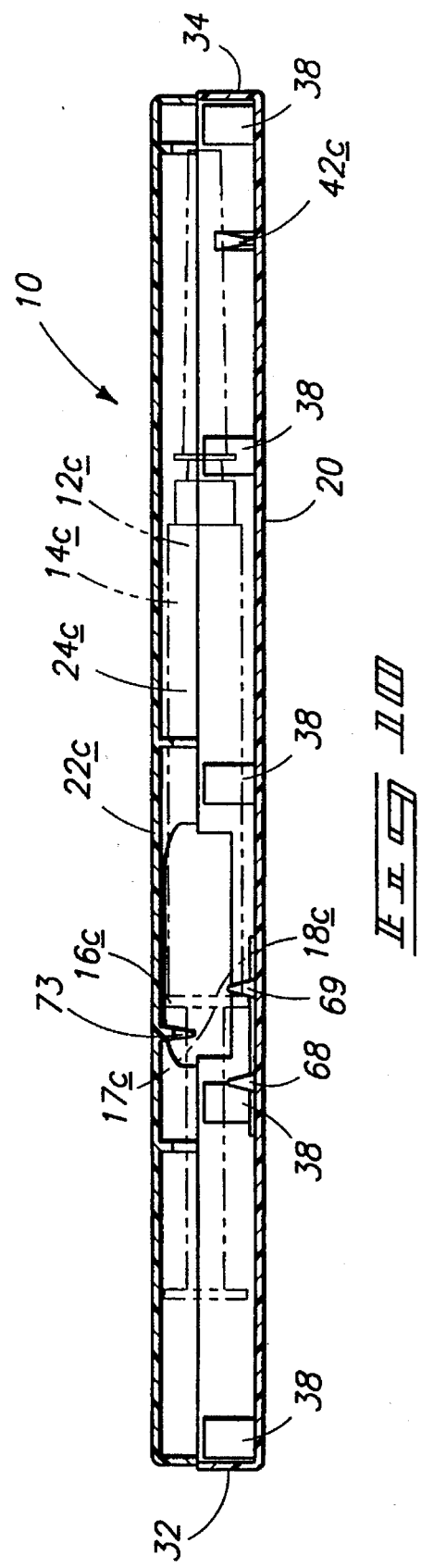

SYRINGE CASE

TECHNICAL FIELD

This invention relates generally to hypodermic syringe cases having at least one compartment sized to contain a hypodermic syringe.

BACKGROUND OF THE INVENTION

Disposable hypodermic syringes for injecting drugs of various kinds have found wide-spread use in the medical and related professions. For out-patient or home delivery of injections, it would be desirable to provide a protective hypodermic syringe case which retains one or more pre-filled hypodermic syringes with the desired medication at the prescribed dose. The case should preferably be easily transportable and safely retain one or more syringes without significant potential for breakage or damage to the syringe.

This invention is directed to improvements in such devices.

BRIEF DESCRIPTION OF THE DRAWINGS

Preferred embodiments of the invention are described below with reference to the following accompanying drawings.

FIG. 5 is a perspective view of a single lid utilized with the syringe case base of FIG. 3.

FIG. 6 is a top view of FIG. 1, however showing only the lids.

FIG. 7 is a diagrammatic sectional view taken through line 7—7 in FIG. 2.

FIG. 8 is a diagrammatic sectional view taken though line 8—8 in FIG. 2.

FIG. 9 is a diagrammatic sectional view taken through line 9—9 in FIG. 2.

FIG. 10 is a diagrammatic sectional view as would be positionally taken through line 9—9 in FIG. 2, but showing the illustrated syringe in phantom at an alternate slid position within the subject compartment.

DETAILED DESCRIPTION OF THE PREFERRED EMBODIMENTS

Figure 1:
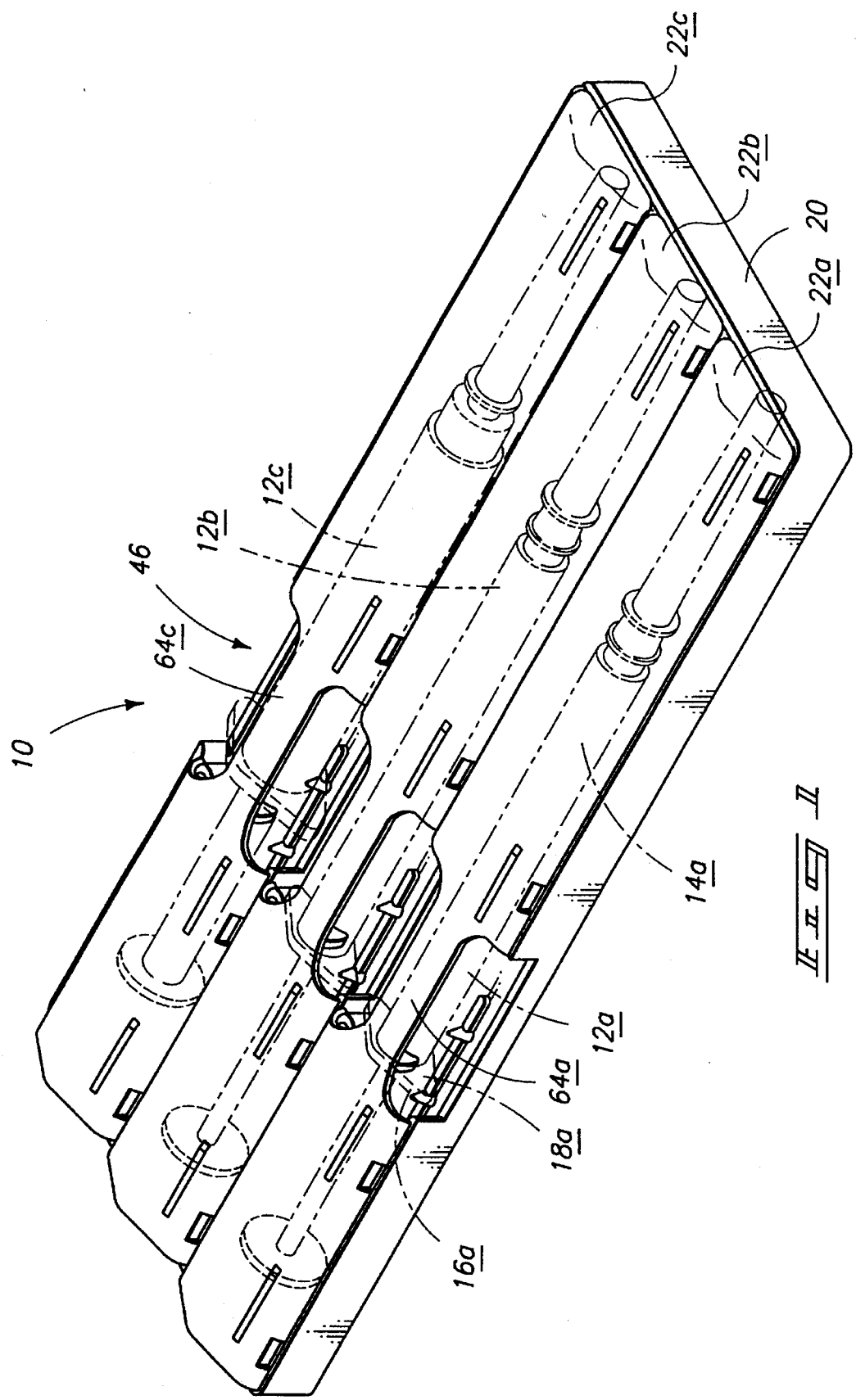
FIG. 1 is a perspective view of a hypodermic syringe case for retaining a plurality of hypodermic syringes.

This disclosure of the invention is submitted in furtherance of the constitutional purposes of the U.S. Patent Laws "to promote the progress of science and useful arts" (Article 1, Section 8).

In accordance with one aspect of the invention, a hypodermic syringe case comprises:

a plurality of longitudinally elongated individual syringe retaining compartments, the syringe compartments having respective lengths which are greater than the length of a syringe for which the respective compartments are adapted;

a separately openable and closable lid associated with the respective syringe compartments;

at least one longitudinal hinge associated with the respective lids and syringe compartments to support the respective lids for longitudinal swinging movement between open and closed positions relative to their respective syringe compartments; and a lid closure latch associated with the respective lids.

In accordance with another aspect of the invention, a hypodermic syringe case comprises:

at least two longitudinally elongated individual syringe retaining compartments, the two syringe compartments having respective lengths which are greater than the length of a syringe for which the respective compartments are adapted, the two syringe compartments being in immediate longitudinally parallel juxtaposition to one another;

a separately openable and closable lid associated with the respective syringe compartments, the respective lids having opposing longitudinal edges and being in longitudinal juxtaposition relative to one another;

a lid closure latch associated with the respective lids and their associated compartments; and the respective lids including respective pairs of recesses provided in their opposing longitudinal edges, one longitudinal edge recess of one of the lids being longitudinally positioned to align with one longitudinal recess of the other lid to provide a finger space between the two juxtaposed lids, the finger space having a size sufficiently great to receive a human finger therewithin.

In accordance with still another aspect of the invention, a hypodermic syringe case comprises:

a longitudinally elongated syringe retaining compartment having a length which is greater than the length of a syringe for which the compartment is adapted;

an openable and closable lid associated with the syringe compartment, the lid having opposing longitudinal edges;

a lid closure latch associated with the lid and compartment; and the lid including a pair of recesses provided in its opposing longitudinal edges, the longitudinal edge recesses being in substantial longitudinal alignment with one another to define a longitudinal lid opening and closing grasping stem.

In accordance with still a further aspect of the invention, a hypodermic syringe case for retaining a syringe comprises:

a longitudinally elongated syringe retaining compartment, the compartment having a substantially planar floor and a length which is greater than the length of a syringe for which the compartment is adapted;

an openable and closable lid associated with the syringe compartment, the lid when closed defining a compartment volume which is sufficiently great to receive a syringe for which the compartment is adapted for sliding longitudinal movement within prescribed limits within the compartment;

the prescribed limits being defined by a pair of opposing lid and floor projections, the floor projection comprising at least one upward projecting member positioned to engage one side of the syringe finger flange of a syringe for which the case is adapted, the lid projection comprising at least one downward projecting member positioned to engage the other side of the syringe finger flange of a syringe for which the case is adapted, the floor and lid projections being longitudinally spaced from one another to define a finger flange receiving space therebetween, the flange receiving space being sufficiently great to slidably receive therewithin the syringe finger flange of a syringe for which the case is adapted; and a lid closure latch associated with the lid and compartment.

More particularly and initially with reference to FIGS. 1–4, a hypodermic syringe case for retaining a plurality of syringes is indicated generally with reference numeral 10. Syringe case 10 is sized for retaining three hypodermic syringes, although syringe cases for two or more syringes are also contemplated. As well, a single syringe retaining case is also contemplated, and described below. Three hypodermic syringes 12a, 12b, and 12c are shown retained by case 10 in FIGS. 1 and 2. Syringes 12a and 12b are of the same construction and size, while syringe 12c is of a larger diametric size to illustrate adaptability of the preferred apparatus to multiple syringe sizes and configurations. For purposes of the continuing discussion and referring only to syringe 12a for simplification, each syringe comprises a fluid retaining barrel 14 having a finger flange 16 positioned adjacent one end thereof. Finger flange 16 has opposing sides 17 and 18. Such are designated with "a" suffixes in FIGS. 1, 2 and 7.

Figure 3:
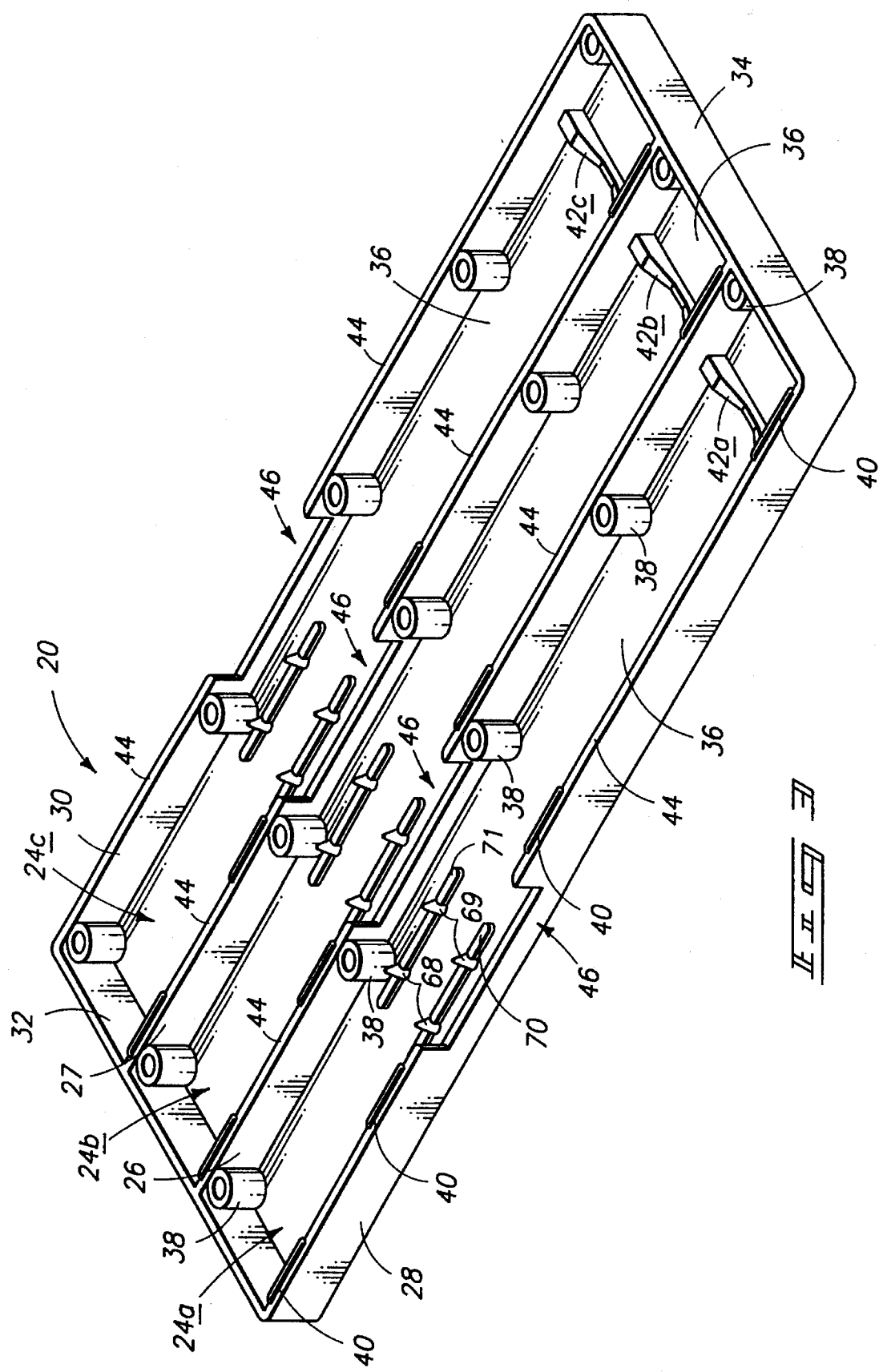
FIG. 3 is a perspective view of the case base of FIG. 1, wherein the lids have been removed and no syringes are shown.
Figure 4:
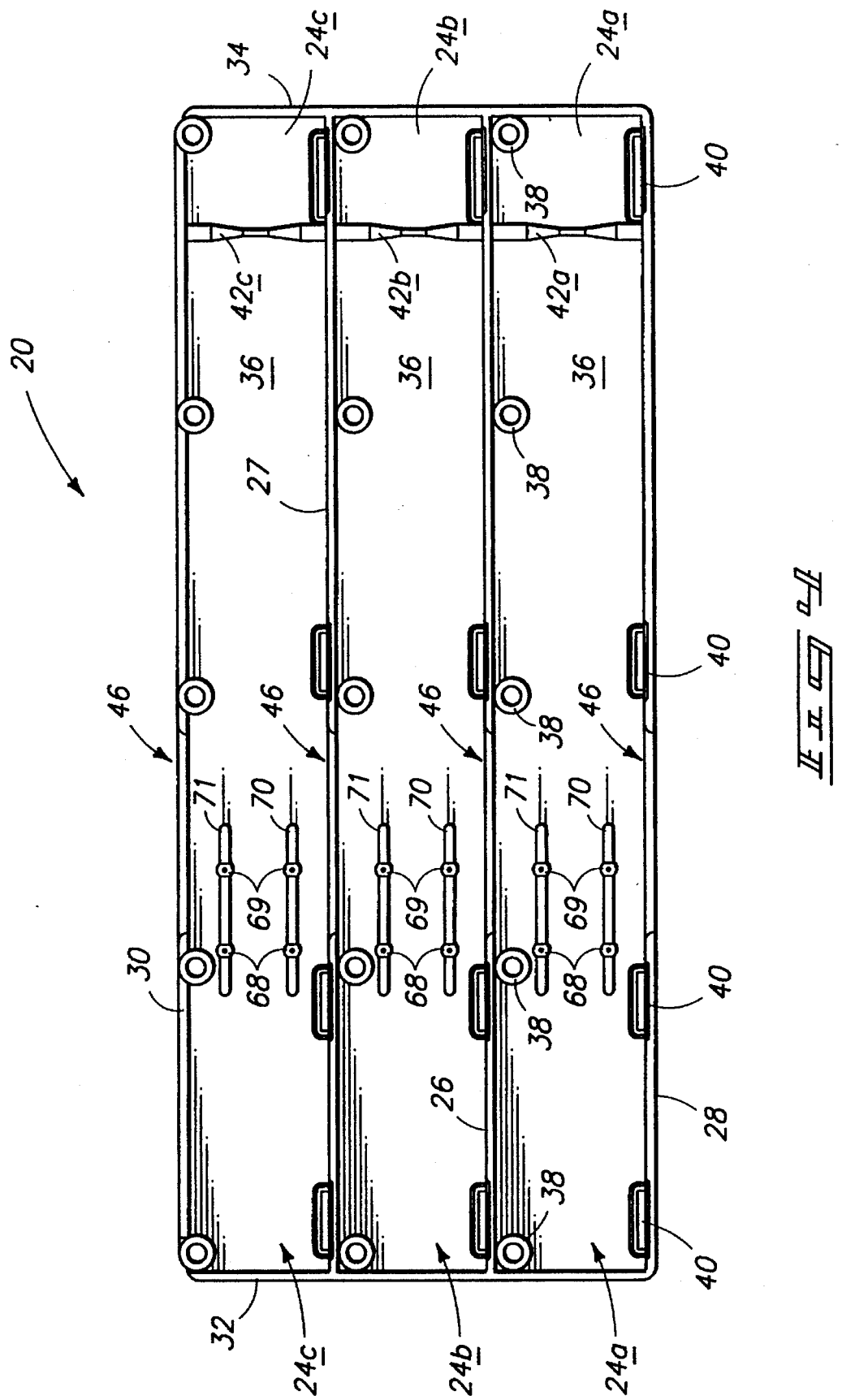
FIG. 4 is a top view of FIG. 3.

Case 10 is comprised of a base 20 and three lids 22a, 22b, and 22c. Case 10 defines three longitudinally elongated individual syringe retaining compartments 24a, 24b, and 24c (FIGS. 3 and 4). Such compartments have respective lengths which are greater than the length of the syringe(s) for which the respective compartments are adapted. Adjacent compartments are in immediate longitudinally parallel juxtaposition to one another, and share respective common longitudinal separating walls 26 and 27 (FIGS. 3 and 4). Remaining portions of the compartments are defined by opposing longitudinal walls 28, 30 and opposing end walls 32 and 34. Separating walls 26 and 27, and end walls 28 and 30, have respective longitudinally aligned and elongated recesses 46 provided therein, as shown. A substantially planar and integral common floor 36 is provided at the base of the illustrated walls.

Each compartment 24 includes a series of five lid pin receiving receptacles 38 aligned along the right longitudinal edge thereof. The opposing left longitudinal edge of each compartment includes four lid latch receiving receptacles 40. Each compartment also includes a respective needle sheath centering gusset 42a, 42b or 42c at the lower end thereof.

One of lids 22a, 22b and 22c is associated to be separately openable and closeable with each syringe compartment 24a, 24b, and 24c, respectively. At least one longitudinal hinge is associated with the respective lids and syringe compartments to support the respective lids for longitudinally swinging movement between open and closed positions relative to their respective syringe compartments. More particularly and with principle reference to FIG. 5, a pair of hinge devices 48 and 49 are integrally formed with each lid 22. Referring to hinge 49, such is comprised of a pair of joined hinge leaves. One hinge leaf is in the form of a longitudinally elongated strip 50, while the other hinge leaf constitutes a main portion 52 of the lid. A series of three integral hinge joining members 53 bendingly interconnect main lid portion 52 with longitudinal strip 50. Thus, the illustrated hinges are formed integrally as part of lids 22. A series of three downwardly projecting pins 54 extend from strip 50, and are sized to be snugly received within case receptacles 38 within each syringe compartment. Thus, a male female interconnection joint is formed relative to the lids 22 and their respective compartments. Hinge 48 is similarly constructed, but with two hinges and joining members.

Main lid portions 52 include a series of four jagged projections 56 which are sized to removably, but snugly, snap fit within latch receptacles 40 associated with each compartment. Thus, a lid closure latch mechanism is associated with each respective lid for retaining it in a closed position with the respective compartments. Reinforcing and aligning gussets 81, 82 and 83 are also provided.

Referring to FIGS. 5 and 6, the respective lids have opposing longitudinal edges 58 and 59. Lids 22 include respective pairs of recesses 61 and 62 provided in their longitudinal edges 58 and 59, respectively. Such define a longitudinally centered and extending grasping stem 64 for each lid. Adjoining or opposing longitudinal edge recesses, such as edge recess 62a and 61b, align with one another to provide a finger space 65 between juxtaposed lids, such as lids 22a and 22b. Finger space 65 is sized to be sufficiently great to receive a human finger or thumb therebetween, as shown. Wall recesses 46 in base 20 are also positioned and sized to longitudinally align with recesses 61 and 62 to, define a portion of the volume of finger spaces 65. Opening and closing of the lids is thereby facilitated.

Lids 22 also include a series of alternate longitudinally elongated raised ribs 66 (FIG. 6) for use as an alternate means of overcoming the latch force imparted by the latch mechanism to open the lid.

The respective lids when closed define respective individual syringe compartment volumes which are sufficiently great to receive a syringe 12 for which the compartment is adapted for sliding longitudinally movement within prescribed limits within the compartment. The limits are defined by a pair of at least one lid projection and at least one opposing floor projection.

More specifically and in the preferred embodiment, the floor projections comprises a first pair of upward floor projecting pins 68 and a second pair of upward floor projecting pins 69. (FIGS. 3 and 4). Such project upwardly from a pair of longitudinally elongated raised ribs 70 and 71. A cradling lid projection 73 extends downwardly from the underside of main lid portion 52 (FIG. 5).

Projections 68 and 69 constitute two pairs of floor projections which are longitudinally spaced from one another and from lid projection 73. This defines a pair of opposing finger flange receiving spaces (two) on opposing longitudinal sides of lid projection 73. With respect to projections 68, such are positioned to opposingly flank the sides of the syringe barrel 14 of syringe 12 for which the case is adapted. The same applies to projections 69. Raised ribs 70 and 71 provide bearing surfaces against which the finger flange 16 of the syringe can bear and freely slide within the prescribed limits.

Figure 2:
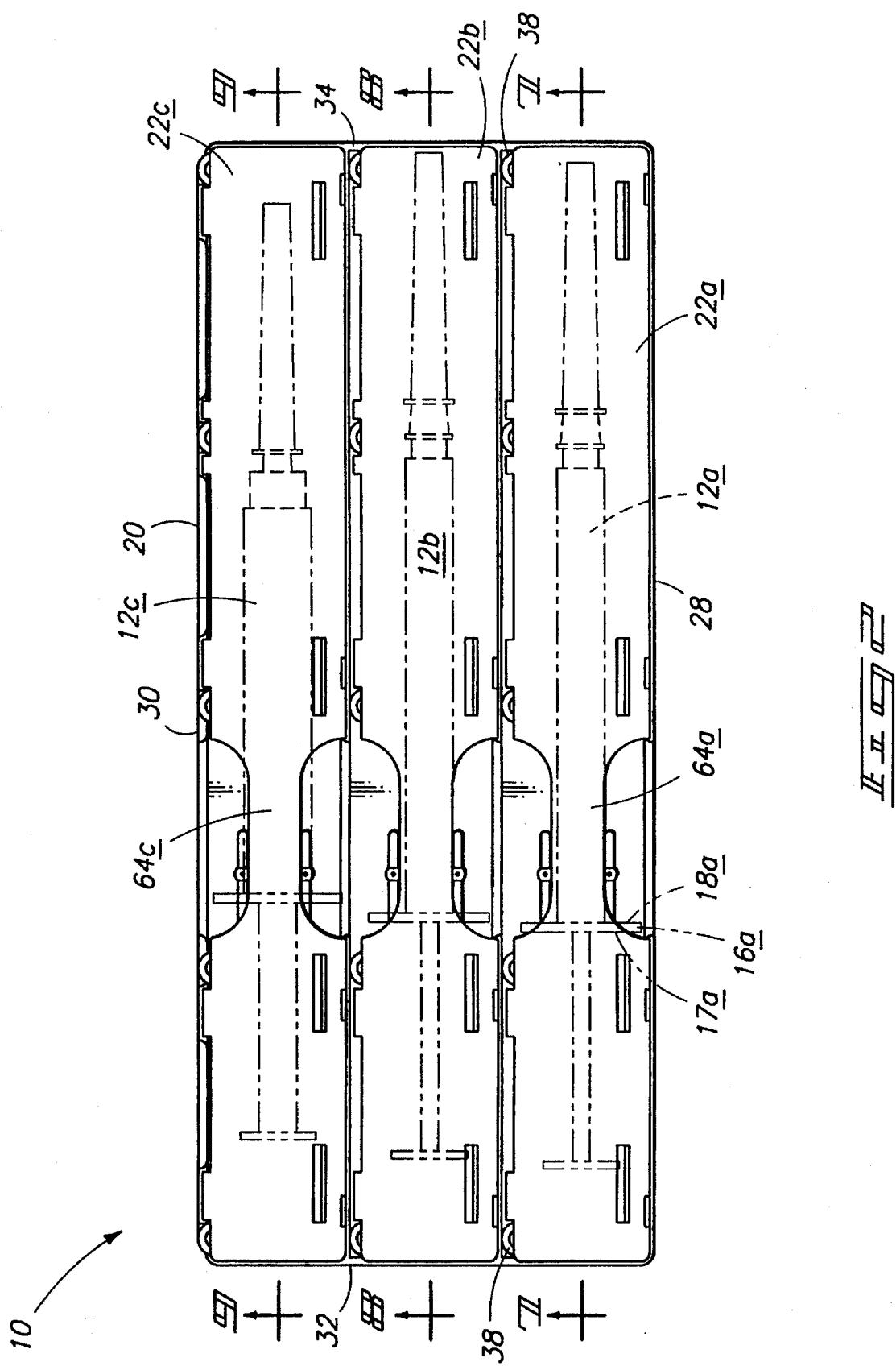
FIG. 2 is a top view of the FIG. 1 syringe case.

The above features will be even more readily understood by referring to FIGS. 2, and 7–10. Specifically and first with respect to FIGS. 2, 7, and 8, syringe 12a is shown slid to its far left prescribed limit (FIGS. 2 and 7), while syringe 12b is shown slid to the far right of its prescribed limits (FIGS. 2 and 8). Accordingly, finger flange face 17a bears against floor projection 68 (FIG. 7), while finger flange face 18b bears against lid projection 73 (FIG. 8). The intervening longitudinal space defined between lid projection 73 and floor projections 68 defines a flange receiving space which is sufficiently great to slidably receive the associated finger flange 16a/16b therewithin for sliding movement within the prescribed limits defined thereby.

FIGS. 2, 9 and 10 illustrate how the device can be utilized to accommodate a different sized syringe. Specifically, finger flange 16c is received in an opposing longitudinal space defined between lid projection 73 and floor projections 69. Accordingly, one longitudinal receiving space is defined between projections 73 and 68, while another syringe flange receiving space is defined between projections 73 and 69. The illustrated syringe 12c is shown to be constructed of a significantly greater diameter syringe barrel 14c than syringes 12a and 12b, such that lid projection 73 is received longitudinally outward beyond the end of flange 16c, effectively over the illustrated syringe 12c plunger stem. The above construction facilitates receipt of various different sized syringes within the same case.

Figure 11:
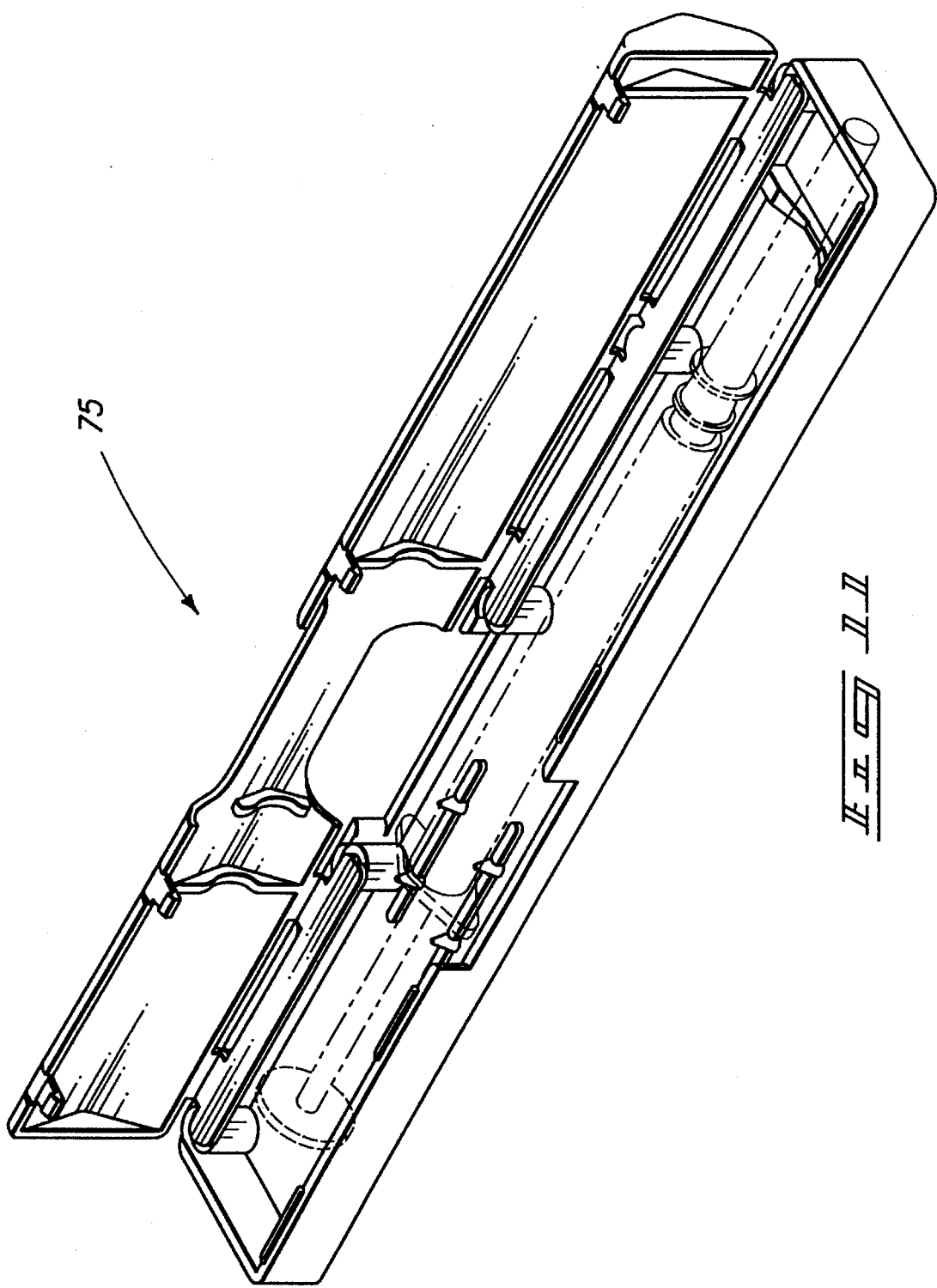
FIG. 11 is a perspective view of an alternate embodiment hypodermic syringe case comprising only a single compartment for containing a single hypodermic syringe.

The artisan will appreciate that the aspects of the invention have applicability to single syringe retaining cases, such as a syringe case 75 shown in FIG. 11. The invention is intended to be limited only by the accompanying claims, appropriately interpreted in accordance with the doctrine of equivalents.

Example materials of construction are polystyrene for the base and polypropylene for the lids.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

I claim:

1. A hypodermic syringe case for retaining a plurality of syringes, the respective syringes having a fluid retaining barrel having a finger flange positioned adjacent one end thereof, the finger flange having opposing sides, the syringe case comprising:

a plurality of longitudinally elongated individual syringe retaining compartments, the syringe compartments having respective lengths which are greater than the length of a syringe for which the respective compartments are adapted, the plurality of compartments including at least two compartments which are in immediate longitudinally parallel juxtaposition to one another, the two juxtaposed compartments being defined in part by a common longitudinal separating wall, the two compartments having substantially planar floors;

a separately openable and closable lid associated with the respective syringe compartments, the respective lids when closed defining respective compartment volumes which are sufficiently great to receive a syringe for which the compartment is adapted for sliding longitudinal movement within prescribed limits within the compartment, the prescribed limits being defined by a pair of opposing lid and floor projections, the floor projection comprising at least one upward projecting member positioned to engage one side of the syringe finger flange of a syringe for which the case is adapted, the lid projection comprising at least one downward projecting member positioned to engage the other side of the syringe finger flange of a syringe for which the case is adapted, the floor and lid projections being longitudinally spaced from one another to define a finger flange receiving space therebetween, the flange receiving space being sufficiently great to slidably receive therewithin the syringe finger flange of a syringe for which the case is adapted;

the respective lids have opposing longitudinal edges, the respective lids including respective pairs of recesses provided in their opposing longitudinal edges, one longitudinal edge recess of one of the lids being longitudinally positioned to align with one longitudinal recess of the other lid to provide a finger space between the two juxtaposed lids, the finger space having a size sufficiently great to receive a human finger therewithin;

the common separating wall having an upper edge, the upper wall edge being downwardly recessed in a longitudinal location where the juxtaposed lid recesses longitudinally align, the wall edge recess in part defining the finger space;

at least one longitudinal hinge associated with the respective lids and syringe compartments to support the respective lids for longitudinal swinging movement between open and closed positions relative to their respective syringe compartments, the hinge comprising a pair of joining hinge leaves and being integrally formed with the lid, the lid comprising one hinge leaf, a longitudinally extending strip comprising the other hinge leaf, the strip leaf joining with the compartment in a male-female interconnection; and a lid closure latch associated with the respective lids.

2. The hypodermic syringe case of claim 1 wherein the floor projection comprises a pair of upward floor projections positioned to flank the syringe barrel of a syringe for which the case is adapted.

3. The hypodermic syringe case of claim 1 comprising a least two floor projections which are longitudinally spaced from one other and the lid projection, the two floor projections and the at least one lid projection defining a pair of opposing finger flange receiving spaces on opposing longitudinal sides of the lid projection.

4. The hypodermic syringe case of claim 1 comprising a least two floor projections which are longitudinally spaced from one other and the lid projection, the two floor projections and the at least one lid projection defining a pair of opposing finger flange receiving spaces on opposing longitudinal sides of the lid projection; and the two floor projections each comprising a pair of upward floor projections positioned to flank the syringe barrel of a syringe for which the case is adapted.

5. A hypodermic syringe case for retaining a syringe, the syringe having a fluid retaining barrel having a finger flange positioned adjacent one end thereof, the finger flange having opposing sides, the syringe case comprising:

a longitudinally elongated syringe retaining compartment having a length which is greater than the length of a syringe for which the compartment is adapted, the compartment being defined in part by a pair of longitudinally opposing walls, the walls having respective upper edges, the compartment having a substantially planar floor;

an openable and closable lid associated with the syringe compartment, the lid having opposing longitudinal edges, the lid when closed defining a compartment volume which is sufficiently great to receive a syringe for which the compartment is adapted for sliding longitudinal movement within prescribed limits within the compartment;

the prescribed limits being defined by a pair of opposing lid and floor projections, the floor projection comprising at least one upward projecting member positioned to engage one side of the syringe finger flange of a syringe for which the case is adapted, the lid projection comprising at least one downward projecting member positioned to engage the other side of the syringe finger flange of a syringe for which the case is adapted, the floor and lid projections being longitudinally spaced from one another to define a finger flange receiving space therebetween, the flange receiving space being sufficiently great to slidably receive therewithin the syringe finger flange of a syringe for which the case is adapted;

at least one longitudinal hinge associated with the lid and syringe compartment to support the lid for longitudinal swinging movement between open and closed positions relative to the syringe compartment, the hinge comprising a pair of joining hinge leaves and being integrally formed with the lid, the lid comprising one hinge leaf, a longitudinally extending strip comprising the other hinge leaf, the strip leaf joining with the compartment in a male-female interconnection;

the lid including a pair of recesses provided in its opposing longitudinal edges, the longitudinal edge recesses being in substantial longitudinal alignment with one another to define a longitudinal lid opening and closing grasping stem, the grasping stem being longitudinally centered between the opposing longitudinal edges;

the respective upper wall edges being downwardly recessed in the longitudinal location where the pair of lid recesses longitudinally align; and a lid closure latch associated with the lid and compartment.

6. The hypodermic syringe case of claim 5 wherein the floor projection comprises a pair of upward floor projections positioned to flank the syringe barrel of a syringe for which the case is adapted.

7. The hypodermic syringe case of claim 5 comprising a least two floor projections which are longitudinally spaced from one other and the lid projection, the two floor projections and the at least one lid projection defining a pair of opposing finger flange receiving spaces on opposing longitudinal sides of the lid projection.

8. The hypodermic syringe case of claim 5 comprising a least two floor projections which are longitudinally spaced from one other and the lid projection, the two floor projections and the at least one lid projection defining a pair of opposing finger flange receiving spaces on opposing longitudinal sides of the lid projection; and the two floor projections each comprising a pair of upward floor projections positioned to flank the syringe barrel of a syringe for which the case is adapted.

9. An assembly comprising:

a syringe having a diameter, and a length perpendicular to the diameter;

a plurality of longitudinally elongated individual syringe retaining compartments, the syringe compartments having respective lengths which are greater than the length of the syringe, one of the syringe retaining compartments housing the syringe;

a separately openable and closable lid associated with the respective syringe compartments;

at least one longitudinal hinge associated with the respective lids and syringe compartments to support the respective lids for longitudinal swinging movement between open and closed positions relative to their respective syringe compartments, the hinge including first and second longitudinally extending hinge leaves integrally formed with the lid, the first hinge leaf being longitudinally spaced apart from the second hinge leaf, the hinge leaves defining respective planar surfaces, the hinge further having a plurality of parallel, longitudinally aligned cylindrical pins extending from respective hinge leaves, and the compartments including respective receptacles receiving the pins; and a lid closure latch associated with the respective lids.

10. The hypodermic syringe case of claim 9 wherein adjacent compartments are defined in part by a common longitudinal separating wall.

11. The hypodermic syringe case of claim 9 wherein, the hinge comprises a pair of joining hinge leaves and is integrally formed with the lid, the lid comprising one hinge leaf, a longitudinally extending strip comprising the other hinge leaf, the strip leaf joining with the compartment in a male-female interconnection; and wherein each longitudinally extending strip is associated with a separate compartment.

12. A hypodermic syringe case comprising:

a plurality of longitudinally elongated individual syringe retaining compartments including at least two compartments which are in immediate longitudinally parallel juxtaposition to one another, the syringe compartments having respective lengths which are greater than the length of a syringe for which the respective compartments are adapted;

a separately openable and closable lid associated with the respective syringe compartments, the respective lids having opposing longitudinal edges, and including respective pairs of recesses provided in their opposing longitudinal edges, one longitudinal edge recess of one of the lids being longitudinally positioned to align with one longitudinal recess of the other lid to provide a finger space between the two juxtaposed lids, the finger space having a size sufficiently great to receive a human finger therewithin;

at least one longitudinal hinge associated with the respective lids and syringe compartments to support the respective lids for longitudinal swinging movement between open and closed positions relative to their respective syringe compartments; and a lid closure latch associated with the respective lids.

13. A hypodermic syringe case comprising:

a plurality of longitudinally elongated individual syringe retaining compartments, the plurality of compartments including at least two compartments which are in immediate longitudinally parallel juxtaposition to one another, the syringe compartments having respective lengths which are greater than the length of a syringe for which the respective compartments are adapted;

a separately openable and closable lid associated with the respective syringe compartments, the respective lids having opposing longitudinal edges and being in longitudinal juxtaposition relative to one another, the respective lids including respective pairs of recesses provided in their opposing longitudinal edges, one longitudinal edge recess of one of the lids being longitudinally positioned to align with one longitudinal recess of the other lid to provide a finger space between the two juxtaposed lids, the finger space having a size sufficiently great to receive a human finger therewithin;

at least one longitudinal hinge associated with the respective lids and syringe compartments to support the respective lids for longitudinal swinging movement between open and closed positions relative to their respective syringe compartments, the hinge comprising a pair of joining hinge leaves and being integrally formed with the lid, the lid comprising one hinge leaf, a longitudinally extending strip comprising the other hinge leaf, the strip leaf joining with the compartment in a male-female interconnection; and a lid closure latch associated with the respective lids.

14. A hypodermic syringe case comprising:

at least two longitudinally elongated individual syringe retaining compartments, the two syringe compartments having respective lengths which are greater than the length of a syringe for which the respective compartments are adapted, the two syringe compartments being in immediate longitudinally parallel juxtaposition to one another;

a separately openable and closable lid associated with the respective syringe compartments, the respective lids having opposing longitudinal edges and being in longitudinal juxtaposition relative to one another;

a lid closure latch associated with the respective lids and their associated compartments; and the respective lids including respective pairs of recesses provided in their opposing longitudinal edges, one longitudinal edge recess of one of the lids being longitudinally positioned to align with one longitudinal recess of the other lid to provide a finger space between the two juxtaposed lids, the finger space having a size sufficiently great to receive a human finger therewithin.

15. The hypodermic syringe case of claim 14 wherein the recesses within the respective pairs are longitudinally aligned with one another.

16. The hypodermic syringe case of claim 14 wherein all of said recesses of all of the lids of the syringe case are longitudinally aligned with one another.

17. The hypodermic syringe case of claim 14 wherein the two juxtaposed compartments are defined in part by a common longitudinal separating wall, the wall having an upper edge, the upper wall edge being downwardly recessed in a longitudinal location where the juxtaposed lid recesses longitudinally align, the wall edge recess in part defining the finger space.

18. The hypodermic syringe case of claim 14 comprising at least one longitudinal hinge associated with the respective lids and syringe compartments to support the respective lids for longitudinal swinging movement between open and closed positions relative to their respective syringe compartments, the hinge comprising a pair of joining hinge leaves and being integrally formed with the lid, the lid comprising one hinge leaf, a longitudinally extending strip comprising the other hinge leaf, the strip leaf joining with the compartment in a male-female interconnection.

19. A hypodermic syringe case comprising:

a longitudinally elongated syringe retaining compartment having a length which is greater than the length of a syringe for which the compartment is adapted;

an openable and closable lid associated with the syringe compartment, the lid having opposing longitudinal edges which define an entire lateral expanse of the lid;

a lid closure latch associated with the lid and compartment; and the lid including a pair of longitudinal edge recesses, each of said longitudinal edge recesses being provided in a separate of said opposing longitudinal edges, the longitudinal edge recesses being in substantial longitudinal alignment with one another to define a longitudinal lid opening and closing grasping stem.

20. The hypodermic syringe case of claim 19 wherein the grasping stem is longitudinally centered between the opposing longitudinal edges.

21. The hypodermic syringe case of claim 19 wherein the syringe for which the case is adapted has a fluid retaining barrel having a finger flange positioned adjacent one end thereof, the finger flange having opposing sides, the syringe case comprising:

the compartment having a substantially planar floor, the lid when closed defining a compartment volume which is sufficiently great to receive a syringe for which the case is adapted for sliding longitudinal movement within prescribed limits within the compartment; and the prescribed limits being defined by a pair of opposing lid and floor projections, the floor projection comprising at least one upward projecting member positioned to engage one side of the syringe finger flange of a syringe for which the case is adapted, the lid projection comprising at least one downward projecting member positioned to engage the other side of the syringe finger flange of a syringe for which the case is adapted, the floor and lid projections being longitudinally spaced from one another to define a finger flange receiving space therebetween, the flange receiving space being sufficiently great to slidably receive therewithin the syringe finger flange of a syringe for which the case is adapted.

22. A hypodermic syringe case comprising:

a longitudinally elongated syringe retaining compartment having a length which is greater than the length of a syringe for which the compartment is adapted, the compartment being defined in part by a pair of longitudinally opposing walls, the walls having respective upper edges;

an openable and closable lid associated with the syringe compartment, the lid having opposing longitudinal edges;

a lid closure latch associated with the lid and compartment; and the lid including a pair of recesses provided in its opposing longitudinal edges, the longitudinal edge recesses being in substantial longitudinal alignment with one another to define a longitudinal lid opening and closing grasping stem, the respective upper wall edges being downwardly recessed in the longitudinal location where the pair of lid recesses longitudinally align, the wall edge recesses in part defining respective finger spaces for receiving a human finger therewithin.

23. A hypodermic syringe case comprising:

a longitudinally elongated syringe retaining compartment having a length which is greater than the length of a syringe for which the compartment is adapted;

an openable and closable lid associated with the syringe compartment, the lid having opposing longitudinal edges;

at least one longitudinal hinge associated with the lid and syringe compartment to support the lid for longitudinal swinging movement between open and closed positions relative to the syringe compartment, the hinge comprising a pair of joining hinge leaves and being integrally formed with the lid, the lid comprising one hinge leaf, a longitudinally extending strip comprising the other hinge leaf, the strip leaf joining with the compartment in a male-female interconnection;

a lid closure latch associated with the lid and compartment; and the lid including a pair of recesses provided in its opposing longitudinal edges, the longitudinal edge recesses being in substantial longitudinal alignment with one another to define a longitudinal lid opening and closing grasping stem.

24. An assembly comprising:

a hypodermic syringe having a fluid retaining barrel including a finger flange positioned adjacent one end thereof, the finger flange having opposing sides;

a longitudinally elongated syringe retaining compartment housing the syringe, the compartment having a pair of opposing end walls, having a substantially planar floor extending between the end walls, and defining a length between the end walls, the length being greater than the length of the syringe, and having a pair of opposing, longitudinally extending side walls;

a pair of parallel, spaced apart, longitudinally extending ribs projecting upwardly from the floor, separate from the side walls and between the side walls, the syringe being housed between the ribs for sliding longitudinal movement;

an openable and closable lid associated with the syringe compartment, the lid when closed defining a compartment volume which is sufficiently great to receive the syringe for sliding longitudinal movement within prescribed limits within the compartment;

the prescribed limits being defined by a pair of opposing lid and floor projections, the floor projection comprising at least one upward projecting member extending from one of the ribs and positioned to engage one side of the syringe finger flange of the syringe, the lid projection comprising at least one downward projecting member positioned to engage the other side of the syringe finger flange of the syringe, the floor and lid projections being longitudinally spaced from the end walls and being longitudinally spaced from one another to define a finger flange receiving space therebetween, the flange receiving space being sufficiently great to slidably receive therewithin the syringe finger flange of the syringe; and a lid closure latch associated with the lid and compartment.

25. The hypodermic syringe case of claim 24 wherein the floor projection comprises a pair of upward floor projections positioned to flank the syringe barrel of a syringe for which the case is adapted.

26. The hypodermic syringe case of claim 24 comprising a least two floor projections which are longitudinally spaced from one other and the lid projection, the two floor projections and the at least one lid projection defining a pair of opposing finger flange receiving spaces on opposing longitudinal sides of the lid projection.

27. The hypodermic syringe case of claim 24 comprising a least two floor projections which are longitudinally spaced from one another and the lid projection, the two floor projections and the at least one lid projection defining a pair of opposing finger flange receiving spaces on opposing longitudinal sides of the lid projection; and the two floor projections each comprising a pair of upward floor projections positioned to flank the syringe barrel of a syringe for which the case is adapted.

28. A hypodermic syringe case for retaining a syringe, the syringe having a fluid retaining barrel having a finger flange positioned adjacent one end thereof, the finger flange having opposing sides, the syringe case comprising:

a longitudinally elongated syringe retaining compartment, the compartment having a pair of opposing end walls, having a substantially planar floor extending between the end walls and defining a length between the end walls, and having a pair of opposing, longitudinally extending side walls;

a pair of parallel, spaced apart, longitudinally extending ribs projecting upwardly from the floor, separate from the side walls and between the side walls to provide a bearing surface for a syringe received therebetween for sliding longitudinal movement;

an openable and closable lid associated with the syringe compartment, the lid when closed defining a compartment volume which is sufficiently great to receive a syringe for which the compartment is adapted for sliding longitudinal movement within prescribed limits within the compartment;

the prescribed limits being defined by a pair of opposing lid and floor projections, the floor projection comprising at least one upward projecting member extending from one of the ribs and positioned to engage one side of the syringe finger flange of a syringe for which the case is adapted, the lid projection comprising at least one downward projecting member positioned to engage the other side of the syringe finger flange of a syringe for which the case is adapted, the floor and lid projections being longitudinally spaced from one another to define a finger flange receiving space therebetween, the flange receiving space being sufficiently great to slidably receive therewithin the syringe finger flange of a syringe for which the case is adapted, the floor and lid projections being longitudinally spaced from the end walls; and a lid closure latch associated with the lid and compartment.

29. A hypodermic syringe case comprising:

a plurality of longitudinally elongated individual syringe retaining compartments;

a separately openable and closable lid associated with the respective syringe compartments;

at least one longitudinal hinge associated with the respective lids and syringe compartments to support the respective lids for longitudinal swinging movement between open and closed positions relative to their respective syringe compartments, the hinge including first and second longitudinally extending hinge leaves integrally formed with the lid, the first hinge leaf being longitudinally spaced apart from the second hinge leaf, the hinge leaves defining respective planar surfaces, the hinge further having a plurality of parallel, longitudinally aligned cylindrical pins extending from respective hinge leaves, and the compartments including respective receptacles receiving the pins; and a lid closure latch associated with the respective lids.

* * * * *